United States Patent
Krause et al.

(10) Patent No.: US 9,233,199 B2
(45) Date of Patent: Jan. 12, 2016

(54) METHOD OF DETECTING RECIRCULATION IN AN ARTERIOVENOUS SHUNT DURING ONGOING HEMODIALYSIS AND DIALYSIS SYSTEM

(71) Applicant: B. BRAUN AVITUM AG, Melsungen (DE)

(72) Inventors: Silvie Krause, Melsungen (DE); Christof Strohhoefer, Kassel (DE); Joern Ahrens, Baunatal (DE); Alex Castellarnau, Melsungen (DE); Soeren Weyer, Aachen (DE)

(73) Assignee: B. BRAUN AVITUM AG, Melsungen (DE)

( * ) Notice: Subject to any disclaimer, the term of this patent is extended or adjusted under 35 U.S.C. 154(b) by 150 days.

(21) Appl. No.: 14/202,727

(22) Filed: Mar. 10, 2014

(65) Prior Publication Data

US 2014/0296766 A1 Oct. 2, 2014

(30) Foreign Application Priority Data

Mar. 28, 2013 (DE) .......................... 10 2013 103 221

(51) Int. Cl.
*A61M 37/00* (2006.01)
*A61M 1/36* (2006.01)
*A61M 1/16* (2006.01)

(52) U.S. Cl.
CPC ............ *A61M 1/3658* (2014.02); *A61M 1/1609* (2014.02); *A61M 1/1615* (2014.02); *A61M 2205/3313* (2013.01); *A61M 2205/3331* (2013.01); *A61M 2205/3334* (2013.01)

(58) Field of Classification Search
CPC ............ A61M 1/3658; A61M 1/1609; A61M 1/1615; A61M 2205/3313; A61M 2205/3331; A61M 2205/3334
See application file for complete search history.

(56) References Cited

U.S. PATENT DOCUMENTS

| 5,507,723 A | 4/1996 | Keshaviah |
| 5,817,042 A | 10/1998 | Langley et al. |

(Continued)

FOREIGN PATENT DOCUMENTS

| DE | 40 24 434 | 2/1992 |
| DE | 195 28 907 | 11/1996 |

(Continued)

OTHER PUBLICATIONS

German Search Report for DE 10 2013 103 221.4 dated Dec. 5, 2013.

(Continued)

*Primary Examiner* — Leslie Deak
(74) *Attorney, Agent, or Firm* — RatnerPrestia

(57) ABSTRACT

Control methods of a dialysis machine for allowing the dialysate-side detection of a recirculation in an arteriovenous shunt of a patient during ongoing hemodialysis are described. A sensor is arranged downstream of a dialyzer and detects a change of a physicochemical parameter $P_D$ of outflowing dialysis fluid. Control elements are provided to guide the dialysis fluid in a selected manner through the dialyzer or pass it by. Recirculation may be determined by passing the dialysis fluid by the dialyzer so that the dialysis fluid is guided unchanged along the sensor for calibration, switching the control elements after optional sensor calibration such that the dialysis fluid flows through the dialyzer, and adjusting a desired first blood flow value $BF_1$ in the blood-side extracorporeal circulatory branch so that between an inlet of the extracorporeal circulatory branch and an outlet a recirculation R and, a first clearance $K_1$ are adjusted and the parameter detected by the sensor adopts a corresponding value $P_{D1}$, changing the first blood flow value $BF_1$ to a second blood flow value $BF_2$, wherein a second clearance $K_2$ is adjusted, and accordingly at the sensor a new parameter value $P_{D2}$ is provided and detected, and determining the recirculation R by the course of change from the parameter value $P_{D1}$ to the parameter value $P_{D2}$.

15 Claims, 15 Drawing Sheets

(56) References Cited

U.S. PATENT DOCUMENTS

| | | | |
|---|---|---|---|
| 6,075,367 A * | 6/2000 | Brugger | A61M 1/16 324/439 |
| 6,117,099 A * | 9/2000 | Steuer | A61M 1/3621 422/44 |
| 6,537,240 B2 | 3/2003 | Cavicchioli et al. | |
| 6,666,840 B1 | 12/2003 | Falkvall et al. | |
| 6,702,774 B1 | 3/2004 | Polaschegg | |
| 7,077,819 B1 | 7/2006 | Goldau et al. | |
| 7,097,630 B2 | 8/2006 | Gotch et al. | |
| 7,674,236 B2 * | 3/2010 | Daniel | A61M 1/16 210/645 |
| 7,815,852 B2 | 10/2010 | Sternby | |
| 8,858,486 B2 | 10/2014 | Zhang et al. | |
| 2005/0133449 A1 | 6/2005 | Sternby | |
| 2010/0276367 A1 * | 11/2010 | Zhang | A61M 1/3658 210/647 |
| 2012/0298581 A1 | 11/2012 | Wehmeyer et al. | |
| 2014/0246373 A1 | 9/2014 | Kopperschmidt | |

FOREIGN PATENT DOCUMENTS

| | | |
|---|---|---|
| DE | 197 02 441 | 2/1998 |
| DE | 695 31 137 | 4/2004 |
| DE | 699 16 053 | 3/2005 |
| DE | 10 2004 023 080 | 12/2005 |
| DE | 10 2006 045 437 | 4/2008 |
| DE | 10 2007 056 475 | 6/2009 |
| DE | 10 2011 102 962 | 11/2012 |
| EP | 0 886 529 | 12/1998 |

OTHER PUBLICATIONS

San Miguel et al., "Vascular dialysis access flow measurement: Early intervention through early detection," J. Renal Care: p. 185-191, 2009.

Krivitski, N.: "Theory and validation of access flow measurements by dilution technique during hemodialysis," Kidney International 48: 244-250, 1995.

* cited by examiner (change of blood flow)
(Effective clearance is shifted with recirculation.
Consequently $level_0$ and $level_R$ are varying)

METHOD OF DETECTING RECIRCULATION IN AN ARTERIOVENOUS SHUNT DURING ONGOING HEMODIALYSIS AND DIALYSIS SYSTEM

CROSS REFERENCE TO RELATED APPLICATIONS

This application claims priority to German application DE 10 2013 103 221.4 filed Mar. 28, 2013, the contents of such application being incorporated by reference herein.

BACKGROUND OF THE INVENTION

The present invention relates to a method of detecting recirculation in an arteriovenous shunt of a patient during ongoing hemodialysis.

Patients suffering from severe kidney insufficiency or kidney failure require dialysis, as is known. For this, the patients concerned have two options of dialysis, on the one hand in a dialysis center of a hospital and, on the other hand, self-dialysis in the domestic area with ambulant dialysis units—after having been introduced by the nephrologist in charge and trained specialized staff—.

For the purpose of the present invention, by the term "dialysis" or "hemodialysis" any chronically applicable blood purification therapy is understood which comprises hemodialysis, hemofiltration and hemodiafiltration.

For performing dialysis in a patient suffering from chronic kidney insufficiency typically a so called arteriovenous shunt constituting a direct connection of an artery to a vein is laid by operation. One of the most frequent shunts laid for dialysis treatment is the so called Cimino shunt in which—after vascular preparation—the radial artery is connected to the cephalic vein.

Such shunt permits a simple vascular puncture for receiving the cannulas required for dialysis and moreover has a sufficient blood flow for performing hemodialysis due to the pressure and flow conditions prevailing in the shunt.

DESCRIPTION OF THE RELATED ART

However, the vascular access in nephrologist circles is considered the Achilles heel of hemodialysis [San Miguel, S & Chow, J: Vascular dialysis access flow measurement: Early intervention through early detection. J Renal Care: 185-191, 2009].

In this context, Australian nephrologists [San Miguel, S & Chow 2009] report about an examination period from November 2006 to May 2007 during which in 35 hemodialysis patients the dialysis accesses were examined by ultrasonography. Out of the group of patients examined, 50% showed a significant shunt stenosis, 11% suffered from thrombosis, 6% had aneurisms, another 6% had problems not specified in detail with their access and merely 19% were without findings.

During dialysis therefore a too low shunt flow and hereby even a so called "recirculation" in the shunt may occur due to the afore-mentioned shunt complications. Recirculation causes the direct reflow of already purified blood from the venous access directly into the arterial access to the dialyser again. This causes a definite reduction of the dialysis efficiency and can be an early indication of a possibly necessary shunt intervention or reconstruction depending on the extent of recirculation.

Since recirculation is resulting in deterioration of the dialysis efficiency and, thus, the patient does not reach his/her objective of treatment, his/her general condition will deteriorate in the long run when unnoticed recirculation is provided. An online measurement which can be carried out automatically by the machine would allow the physician, if a present shunt recirculation is suspected, to immediately verify or falsify the same.

Equally an automatically performed measurement, e.g. prior to each dialysis therapy, can draw the attention of the physician or the nursing staff to the presence of a shunt recirculation. Recirculation can result from two different reasons: An error in connecting the patient to the dialyser or, as explained, a degeneration of the shunt. The first type of recirculation usually can be easily corrected by the medical staff after being informed by the dialysis system. In the second type, the measurement of the recirculation by the dialyser can provide the physician with valuable information for taking further steps.

The recirculation R is defined as the ratio of the flows of recirculated blood Qr and blood pump rate Qb (cf. FIG. 2) and is indicated in %:

$$R = \frac{Qr}{Qb}$$

For measuring the recirculation the state of the art provides a number of approaches:

For instance, KRIVITSKI 1995 describes the theory and the validation of flow measurements in the dialysis access by means of a dilution technique by bolus injection of physiological saline solution into the blood flow of the access of a patient and measurement of the blood protein dilution by Doppler ultrasonography [Krivitski, N: Theory and validation of access flow measurements by dilution technique during hemodialysis. Kidney International 48: 244-250, 1995]. The technique of KRIVITSKI 1995 is based on the detection of different sonic velocities of the blood and the physiological NaCl solution.

Furthermore, the document EP 0 886 529 B1 (Gambro Hospital) describes an apparatus for determining the blood recirculation in a vascular access of a dialysis system by measuring the hemoglobin concentration in the extracorporeal blood circulation of the dialyser.

U.S. Pat. No. 7,815,852 B2 (Gambro Lundia) discloses the measurement of a cardiovascular parameter by bolus injection on the blood side and bolus detection on the dialysate side in the dialysate drain.

Moreover, DE 197 02 441 C1 (Fresenius Medical Care) describes a method of determining the recirculation during extracorporeal blood treatment using a concentrate bolus on the dialysate side.

Furthermore, DE 195 28 907 C1 (Fresenius AG) discloses a measuring method for determining recirculation while making use of system changes caused by short-term reversal of the blood flow in the dialyser.

DE 10 2007 056 475 A1 (Fresenius Medical Care) describes a method and the pertinent apparatus for determining recirculation in a fistula, wherein the recirculation is determined by variation of a chemical-physical measured variable in two different blood flows by measurement on the blood side of the dialyser. As a preferred method a thermodilution method is disclosed in DE 10 2007 056 475 A1. The recirculation is detected in these dialysers by temperature control (blood temperature monitor) of the blood and by the bolus supply of a temperature pulse.

With the aid of a hematocrit sensor it is equally possible to determine recirculation by way of a bolus on the blood side.

Although all afore-mentioned methods basically allow information as to quality and quantity of the recirculation in the vascular access of the dialysis patient, the methods according to the state of the art have a number of drawbacks, however:

The temperature dilution method is susceptible to outer influences such as ambient temperature. Since a tubular path is provided between the measuring position and the patient, the measurement can be falsified at these points by loss of energy or introduction of energy. Further falsification can be brought about by the interaction of the thermal bolus and the patient's temperature, as the bolus has to pass the shunt and the cardiopulmonary circulation. Moreover, as a rule two sensor modules and thus expensive technical equipment are necessary to make arterial and venous measurements which renders dialysers making use of this method more expensive.

The afore-described blood flow reversal during the ongoing dialysis is hardly recommendable, from the medical point-of-view, because of the additional risk of error of an unintentional confusion of the arterial and venous lines during routine operation.

Detecting the recirculation by means of Doppler ultrasonography requires extremely expensive technical equipment and in addition a saline solution bolus has to be manually administered. The drawback of the manual bolus administration is also applicable to the hematocrit detection by an external instrument which moreover incurs high acquisition costs.

SUMMARY OF THE INVENTION

Based on the state of the art of bolus methods for determining recirculation, it is therefore an object of the present invention to provide a method and an apparatus for fully automatic measurement of an access recirculation in a patient requiring dialysis.

In particular, the present invention relates to a dialysis machine control method for the machine-side (not patient-side) detection of recirculation in an arteriovenous shunt of a patient preferably during ongoing hemodialysis by means of the dialysis machine itself, wherein the dialysis machine or the dialysis system has a side facing away from the patient (dialysis fluid side) and a side facing the patient (blood side);

wherein on the dialysis fluid side of the dialysis system at least one dialysis fluid inlet as well as at least one dialysis fluid discharge for a selected dialysis fluid and at least one fluid/dialysis fluid pump are provided which are in fluidic communication with at least one dialyser having a semipermeable membrane that forms the boundary between the dialysis fluid side and the blood side; and wherein the dialysis fluid on the dialysis fluid side of the membrane flows through a dialysis fluid chamber of the dialyser in a predetermined direction;

wherein on the blood side of the dialysis system in an extracorporeal circulatory branch a blood pump is provided which is adapted to guide blood through a blood chamber of the dialyser so as to remove uremic toxins by diffusion via the semipermeable membrane from the extracorporeal-guided blood;

wherein a sensor for detecting a change of a physicochemical parameter $P_D$ of the outflowing used dialysis fluid is provided in the distal fluidics; and control elements are arranged in the distal fluidics so that the dialysis fluid is optionally guided unchanged through/along the sensor before entry into the dialyser chamber; thereby the sensor being calibrated with unused (pure) dialysis fluid;

and wherein the control elements are set after calibration so that the dialysis fluid flows through the dialyser chamber and in the blood-side extracorporeal circulatory branch a desired first blood flow value $BF_1$ is set, thereby a recirculation R occurring between an inlet of the extracorporeal circulatory branch and an outlet of the extracorporeal circulatory branch and the parameter detected by the sensor adopting a value $P_{D1}$;

the first blood flow value $BF_1$ is changed to a second blood flow value $BF_2$, wherein a new parameter value $P_{D2}$ is provided and detected at the sensor;

and the course of change (or the change) from $P_{D1}$ to $P_{D2}$ is used to detect or determine the recirculation in response to the way of the course of change (of the change). It is outlined in the context that the recirculation is zero or negligible, respectively, or at least known for at least one out of the first and second blood flow values.

Moreover, the present invention relates to a dialysis machine or a dialysis system comprising a means for detecting recirculation in a blood inlet/outlet element, preferably an arteriovenous shunt, of a patient during ongoing hemodialysis, wherein the dialysis system has a side facing away from the patient (dialysis fluid side) and a side facing the patient (blood side);

wherein on the dialysis fluid side of the dialysis system at least one dialysis fluid inlet as well as at least one dialysis fluid discharge for a selected dialysis fluid and at least one dialysis fluid pump are provided, the latter being in fluidic communication with at least one dialyser having a semipermeable membrane which forms the boundary between the dialysis fluid side and the blood side; and wherein the dialysis fluid on the dialysis fluid side of the membrane flows through a dialysis fluid chamber of the dialyser in a predetermined direction;

wherein on the blood side of the dialysis system blood can be guided in an extracorporeal circulatory branch by means of a blood pump preferably in a direction opposite to the flow direction of the dialysis fluid through a blood chamber so as to remove uremic toxins especially by diffusion through the semipermeable membrane out of the extracorporeal-guided blood;

wherein at least one sensor for detecting a change or a course of change of a physicochemical parameter $P_D$ (e.g. absorption, absorbance etc.) of the outflowing used dialysis fluid is provided in the distal fluidics; and preferably control means are arranged in the distal fluidics so that the dialysis fluid flows unchanged through/along the sensor in a selected manner before entering the dialyser chamber so as to further preferably perform calibration of the sensor with pure/unused dialysis fluid;

the control means can be set/are set after (optional) calibration so that the dialysis fluid flows through the dialyser chamber and in the proximal extracorporeal circulatory branch a desired first blood flow value $BF_1$ can be set/is set, whereby between the inlet of the extracorporeal circulatory branch and an outlet of the extracorporeal circulatory branch recirculation R occurs and the parameter detected by the sensor has a value $P_{D1}$;

the first blood flow value $BF_1$ can be changed (for example in a jump-like, ramp-like manner etc.) to a second blood flow value $BF_2$ (preferably by means of a blood pump), a new second parameter value $P_{D2}$ being provided at the sensor; and means are provided for detecting the course of change and/or the change from $P_{D1}$ to $P_{D2}$ and for determining the recirculation R therefrom.

A preferred method is such in which an optical absorption, especially absorption in the IR wavelength range, UV wavelength range or in the visible wavelength range, or an adequate absorbance is employed as physicochemical parameter $P_D$.

In practice it has turned out to be advantageous to use UV absorption and/or UV absorbance as physicochemical parameter $P_D$. In particular LED are used which emit UV light at a wavelength of approx. 280 nm. Expediently, for detection of the absorption as to quantity (absorbance) a UV detector is used as sensor. The advantage of the wavelength range used is that substances usually eliminated with the urine show good absorptions within this range, whereby high sensitivity can be obtained while making use of standard components.

In a preferred embodiment of the method according to aspects of the invention, the second blood flow value $BF_2$ is (preferably considerably) lower than the first blood flow value $BF_1$, wherein especially $BF_2 = r \times BF_1$ is applicable, preferably with r=0.05 to 0.95. That is to say, the value $BF_2$ can be definitely or even only minimally lower than the value $BF_1$, namely further preferably depending on the operating range of the currently used blood pump.

By such condition the blood flow can be set to a value lying below the natural shunt flow. In such case, the recirculation in the shunt is zero as an excellent approximation so that, when recirculation is provided, an easily detectable change is resulting for the physicochemical parameter in the dialysis blood flow set for therapy.

However, it can also be beneficial to tread the inverse path in which the second blood flow value $BF_2$ is (preferably considerably) higher than the first blood flow value $BF_1$, wherein especially $BF_2 = r \times BF_1$ is applicable, preferably with r=1.05 to 20, namely equally preferably in response to the currently used blood pump. In this case, the preferred operating range of the blood pump would be (as also in the aforementioned indication) between 30 ml/min and 600 ml/min. In this context, it is expressly referred to the fact, however, that said operating range of the blood pump can also be fixed to a different value, wherein then depending hereon the difference between the two blood flow values would be determined differently (i.e. outside the afore-mentioned ranges).

A further preferred embodiment of the method according to aspects of the invention is characterized in that the recirculation R is detected by a transient behavior of the time course of the change of the physicochemical parameter $P_D$ after change of the first blood flow $BF_1$ to the second blood flow $BF_2$.

By such transient analysis it is achieved that the present invention provides reliable data of recirculation as to quantity and/or quality during dialysis without requiring any external measures such as bolus injections.

A preferred implementation of the transient analysis is a method in which the transient behavior is detected by a damping δ and by means of the damping δ (delta) of the transient behavior after applying the second blood flow $BF_2$ the recirculation R is determined by an appropriate algorithm explained in detail in the examples.

The transient analysis can alternatively be implemented in that the transient behavior is detected after applying the second blood flow $BF_2$ by integration of a normalized time signal, especially having an intensity output by the sensor, over a defined period of time and in this way the recirculation R is determined by an appropriate algorithm explained in detail in the examples.

The transient analysis can further be alternatively implemented in that the transient behavior is detected after applying the second blood flow $BF_2$ by a characteristic time τ of a signal increase in the output signal provided by the sensor and hereby the recirculation R is determined by an appropriate algorithm explained in detail in the examples.

A particular advantage of the different methods of transient analysis is substantiated in the fact that the results of at least two different methods for forming a mean value are used to carry out plausibility tests and/or to increase the accuracy.

For monitoring the pressure conditions, the current operation and the correct connection of the blood inlet/outlet element, preferably shunts at the proximal side of the dialysis system, in the dialysis system pressure sensors can be provided for the dialyser in the proximal circulation for the arterial pressure (PA), the venous pressure (PV) and the input pressure (pressure before entrance [PBE]). If an evaluation of the pressure sensors exceeds or falls below pre-programmed thresholds, pre-programmed control measures are initiated where appropriate.

With the aid of the present invention it is possible to perform measurement for determining the recirculation in the shunt without influencing the blood side by a bolus. Thus it is possible to perform punctual measurements without additional measuring instruments being required.

Therefore, the method and the apparatus according to the present invention offer the following advantages:

The situation at the patient's access can be monitored online

No bolus injection has to be used

A transient signal measured by means of a sensor on the dialysate side is analyzed after change of the system condition Preferably an optical sensor, especially an UV sensor, can be used The invention permits continuous monitoring of the shunt situation by storing and evaluating the trends of the measurements An automatic recirculation detection after triggered measurement can be carried out during the ongoing therapy Short measuring time of less than 4 min is provided The method and the apparatus are inexpensive as a sensor system provided anyway can be used Little technical equipment required Measurement is carried out on the dialysis fluid side so that no interaction of the sensor with the patient's blood occurs so that no microbiological contamination has to be feared By measurement on the dialysis fluid side the nursing staff does not have additional work with preparing the dialysis system and inserting the blood tube system into the sensors Measurement requires no staff-intensive step.

BRIEF DESCRIPTION OF THE DRAWINGS

The invention is best understood from the following detailed description when read in connection with the accompanying drawings. Included in the drawings are the following figures.

DETAILED DESCRIPTION

It is the target of this invention to enable measurement without a bolus administration. In parallel to this, no additional technical equipment shall be necessary and thus the invention shall be based on a sensor system which is already provided (anyway) in a generic dialysis apparatus.

Figure 1:
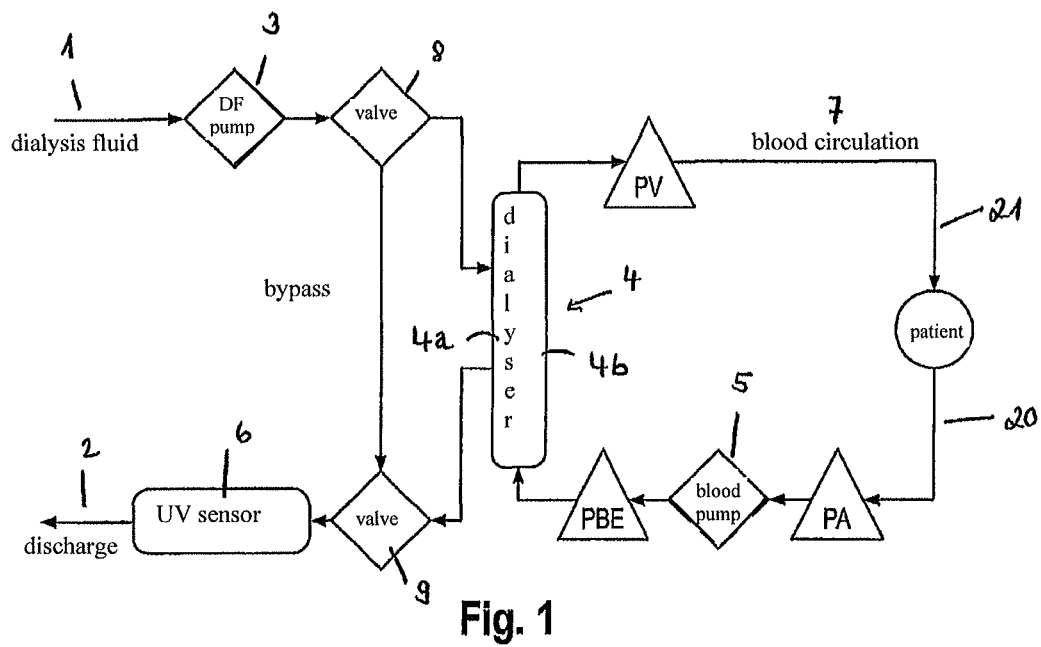
FIG. 1 shows a schematic representation of the fluidics of an exemplary dialysis system according to the present invention.

In the flow diagram of FIG. 1 a dialysis system according to aspects of the invention having a side facing away from the patient (dialysis fluid side) and a side facing the patient (blood side) is shown in schematic representation.

By 1 a dialysis fluid inlet is denoted and by 2 a dialysis fluid discharge is denoted. Via a flow pump 3 dialysis fluid is pumped into a dialysis fluid chamber 4a of a dialyser 4 so that the dialysis fluid flows through the chamber 4a in a predetermined direction. The dialyser 4 includes a semipermeable membrane not shown in FIG. 1 which forms the boundary between the distal side and the proximal side of the dialyser 4. Furthermore the dialyser 4 has a blood chamber 4b on the proximal side.

At the dialysis fluid discharge 2 a UV detector is arranged as sensor 6. For calibrating the UV sensor 6 with pure dialysis fluid valves 8 and 9 are arranged upstream and downstream of the dialysis fluid chamber 4a as control means/elements which can be set so that pure dialysis fluid flows via a bypass formed by the valves 8 and 9 and not through the dialyser chamber 4a.

On the blood side of the dialysis system blood to be purified is pumped from an arteriovenous shunt of a patient from an entry 20 of the extracorporeal circulatory branch by means of a blood pump 5 and a preset blood flow, in the exemplary case preferably 200 ml/min, through the blood chamber 4b further preferred in the reverse flow to the dialysis fluid, wherein a defined first clearance of the membrane-permeable substances usually eliminated with the urine is brought about and hereby the natural kidney function is largely imitated and thus the (arterial) blood of the patient is purified. From the blood chamber 4b purified (venous) blood flows via an outlet 21 of the extracorporeal circulation back to the patient. A typical hemodialysis takes several hours. For monitoring and controlling the entire dialysis method, on the blood side a sensor PV for the venous pressure, a sensor PA for the arterial pressure as well as a sensor PBE (pressure before entrance) for the pressure at the entrance of the blood chamber 4b are arranged.

1. The UV Measuring Method

The UV measuring method itself is described in the German patent specification DE 699 16 053 T2 (Althin Medical AB) the full content of which is herewith referred to. However, hereinafter the UV measuring method applied within the scope of the present invention is briefly described:

In order to ensure an adequate dialysis treatment according to DE 699 16 053 T2 the so called Kt/V (urea model) was developed, wherein K is the capability of the dialyser of removing urea in ml/min from the blood, t is the treatment duration in minutes and V denotes the distribution of urea in the body in ml related to the body weight of the patient. The dimensionless factor Kt/V (urea) defines the elimination of the urea nitrogen content in the blood and can be more than or equal to 1 for three treatments each week, for example.

The measuring principle of the UV sensor for determining the Kt/V of the afore-mentioned patent specification is based on the principle of photometry.

The light source consists of an LED and two photo-detectors, for example, serve as detectors. The LED emits a signal having a wavelength of approx. 280 nm. This wavelength is absorbed by substances to be eliminated with the urine.

The sensor 6 is provided in the dialysate discharge 2 behind the dialyser 4 and during therapy continuously measures the absorption A (intensity) in the dialysis fluid discharge 2.

At the beginning the detector$_0$ value is established with pure dialysis fluid for $$A = \log_{10}\left(\frac{Detektor_0}{Detektor_i}\right)$$

calibration.

In this case the detector0 value is the level calibrated in the beginning which is carried out with a substance, usually the unused dialysis fluid, without the (toxic) substances to be measured. Therefore, the calibration is performed before connecting the patient or in the bypass via valves 8 and 9.

The dialysis fluid flow, the blood flow BF and the dialyser 4 used influence the absorption and thus the prevailing clearance which is relevant to the absorption in the dialysis fluid flow 2. The removed toxins are diluted from the blood side (clearance) by the dialysis fluid flow and the absorption is measured in the dialysis fluid discharge 2. The UV sensor 6 and the pressure sensors PV, PA and PBE are accommodated in tubes as shown in FIG. 1.

2. Detection of Recirculation in the Shunt

If recirculation occurs in the shunt, already purified blood from the venous access is partially transferred to the arterial access again. Recirculation R in [%] is the ratio between purified blood and the actual blood flow. In this way, it is not the actual concentration of toxins existing in the patient that is conveyed to the dialyser but only a dilution with already purified blood, thereby the dialysis efficiency being reduced.

Figure 2:
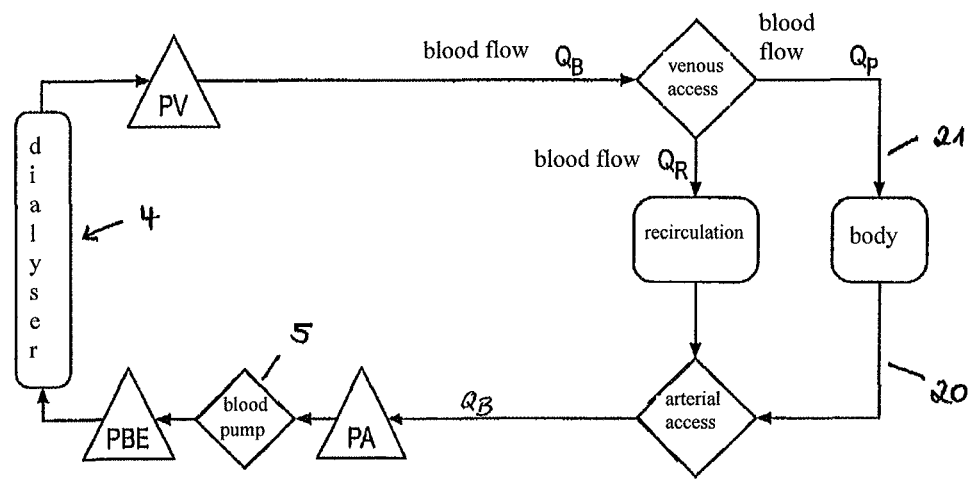
FIG. 2 is a schematic representation of the fluidics of a proximal side of a dialysis system with recirculation in the shunt during therapy.
Figure 3:
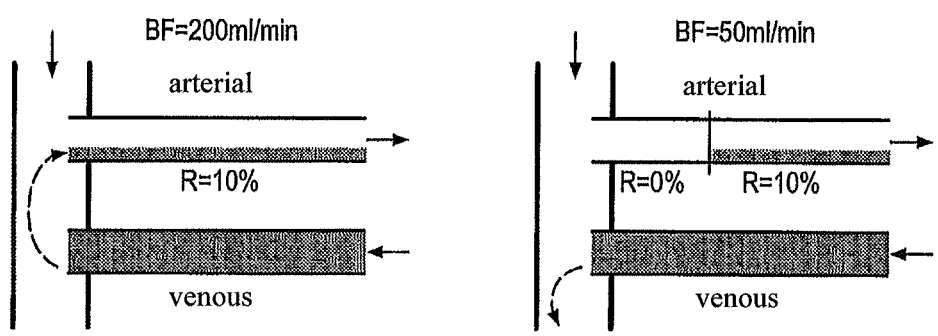
FIG. 3 is a schematic representation of recirculation with different blood flows.

In FIG. 2 recirculation in a shunt during dialysis therapy is shown in schematic representation. The following $$Rezirkulation\ R\ [\%] = \frac{Q_R}{Q_B}$$

$$Q_B = Q_R + Q_P$$

is applicable, wherein $Q_R$ is the flow of recirculating blood, $Q_B$ is the blood flow in the extracorporeal circulation, i.e. corresponds to the flow set at the blood pump 5 and $Q_P$ is the blood flow in the shunt of the patient.

3. Method of Determining Recirculation in the Shunt by a Change of the Blood Flow and Evaluation of the Transient Phenomenon In order to measure recirculation in the shunt the method consists of different intervals which allow for carrying out the determination without external influences (especially on the patient's side).

Recirculation in this context means the part in the extracorporeal blood circulation which is already purified and received/returned again from the venous branch and thus reduces the efficient dialysis performance. The approach is based on the fact that by a reduction of the blood flow the recirculation is also reduced. If the blood flow is smaller than or equal to the shunt flow, ideally no more recirculation occurs.

Within the scope of the present invention, this background is utilized to detect the part of recirculation (merely) by the change of the blood flow.

The set dialysis blood flow in the therapy thus has a constant recirculation depending on the shunt flow. In this way a concentration of uremic toxins diluted compared to the concentration in the patient's blood is provided in the extracorporeal blood with a diluted concentration being related to the actual concentration in the intracorporeal blood circulation of the patient.

By changing the blood flow to a value smaller than (e.g. 50 ml/min) or equal to the shunt flow the clearance at the dialyser is varied.

[cf. KF KDOQI Guideline 3. Methods for postdialysis blood sampling. [Internet]. [cited 2009 Aug. 18]; available from: http://www.kidney.org/professionals/KDOQI/guideline_upHD_PD_VA/hd_guide3.htm]

Hence the concentration of uremic toxins is transient at the outlet of the dialyser 4 to a new level which is dependent on the newly adjusting clearance. If in a first (determined/set) blood flow $BF_1$ of the therapy already recirculation is provided, blood having a concentration of uremic toxins C1 is provided in the arterial access 20 of the tubing system, wherein in the patient blood has a concentration of uremic toxins of C0. The difference of the two concentrations C1 and C0 is caused by the recirculation.

In the case of change to a smaller second (determined) blood flow $BF_2$, for example, which is assumed to be smaller than the shunt flow, no more recirculation does exist. In this way after short time the blood absorbed into the tubing system (extracorporeal blood circulation) again has the concentration C0 corresponding to the blood in the patient. After changing the blood flow, however, blood having the concentration C1 is still provided in the tubing system and is now purified by the new second blood flow $BF_2$ and thus also by the new clearance $K_2$.

If no recirculation has been provided before, C1=C0 is applicable. The transient phenomenon in this case occurs without overshooting to the new level L2.

If the first blood flow $BF_1$>shunt flow, the transient phenomenon shows overshooting, however, because recirculation is provided. In other words, an overshooting takes place because when the blood flow is reduced, blood having the concentration C1 is still provided in the extracorporal tubing system which, however is now purified by the new clearance. The intensity of such overshooting phenomenon is thus directly proportional to the recirculation.

3.1 the Mathematic Determination of Recirculation by Means of a Transient Method after Change of the Blood Flow Via the Damping δ (Delta)

By determining the transfer function from the recorded curve trace the parameters of the function F(s) are established. This characterization of the curve trace forms the basis of calculating the recirculation.

Figure 4:
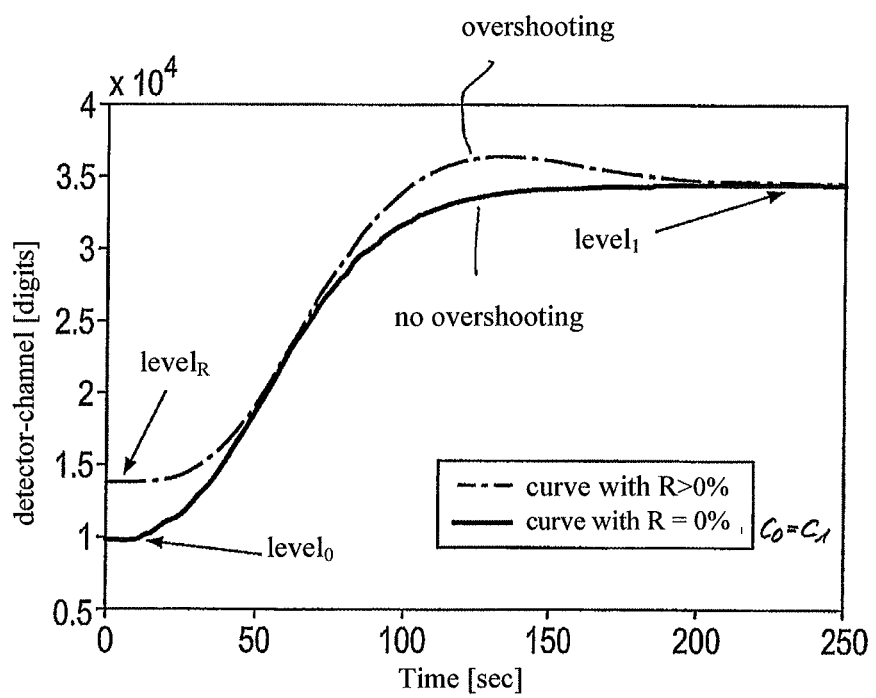
FIG. 4 is a diagram of a transient phenomenon of a detected signal with and without recirculation (from level 0 to level 2)

Possible curve traces are depicted in FIG. 4 showing the transient phenomenon with and without recirculation. The blood concentration in both cases is equal to C0. The different level at the beginning is equally directly proportional to the recirculation, as for this reason the concentration C1 in the tubing system is different and is directly transmitted by reason of the same dialyser clearance. In both measurements the same dialyser clearance exists for the level 0 and the level R due to an equal blood flow BF according to FIG. 4. Said dialyser clearance forms the transfer function between the blood side and the dialysis fluid side.

$$C_B \cdot K = C_D \cdot Q_D$$

$$A_{D\_i} = \log \frac{Det_0}{Det_i}$$

$$A_{D\_i} \sim C_{D\_i}$$

Due to the recirculation in the shunt, the concentration in the extracorporeal blood tubing system is C1<C0 and thus equally the detector signal level R is higher, because fewer substances are removed with the same clearance $K_1$. If no recirculation exists, C1=C0 is applicable.

The characterization of the transfer function can be described in general by the following equation.

$$F(s) = \frac{N(s)}{P(s)}$$

$$F(s) = \frac{s^i + n_1 \cdot s^{i-1} + \ldots + n_{i-1} \cdot s + n_i}{p_0 \cdot s^j + p_1 \cdot s^{i-1} + \ldots + p_{j-1} \cdot s + p_j}$$

By way of example, the step response of a transfer function known as PT3 control distance can be chosen to characterize the phenomenon. The PT3 control distance has the following form:

$$F(s) = \left( \frac{1}{T^2 \cdot s^2 + 2 \cdot \delta \cdot T \cdot s_1} \right) \cdot \left( \frac{1}{s+c} \right)$$

wherein the operator s stands for the derivation operator $$s = \frac{d}{dt}.$$

A general calculation is possible by determining the poles. For this, from the transfer function determined before the poles are determined $$Polpaar_{konjugiert\_konplex} = -\frac{\delta}{T} \pm \sqrt{\left(\frac{\delta}{T}\right)^2 - \frac{1}{T^2}}$$

(Pair of $poles_{conjugated\_complex}$)

$$a = \frac{\delta}{T}$$

$$b = \sqrt{\left(\frac{\delta}{T}\right)^2 - \frac{1}{T^2}}$$

$$F(s) = \left(\frac{1}{(s+a+bj)\cdot(s+a-bj)\cdot(s+c)}\right)$$

and with the aid of the complex pair of poles the damping δ is calculated.

$$\delta = \left|\left(\frac{\text{Re}\{Polpaar\}}{|Polpaar|}\right)\right|$$

Apart from the transient behavior by the volumes in the dialyser 4, the parameter δ describes the damping.

If during the change of the blood flow in the tubing system (extracorporeal blood circulation) the system has the blood concentration of $C_R = C_0$, the parameter is δ~1. It is mentioned in this context that according to FIG. 5 the damping can also be (slightly) lower or higher than 1 for the case free of recirculation dependent on the dialyser used.

In the case of an existing recirculation and thus $C_1 < C_0$, the system is overshooting and thus δ decreases proportional to the recirculation. The determination of R is thus possible directly from the determined damping δ and is determined by the following correlation.

The gradient of the function in this case is dependent on the blood flow of the transient level and hence equally from the clearance. In this way, for each blood flow a function is resulting by which the recirculation R is determined.

Figure 5:
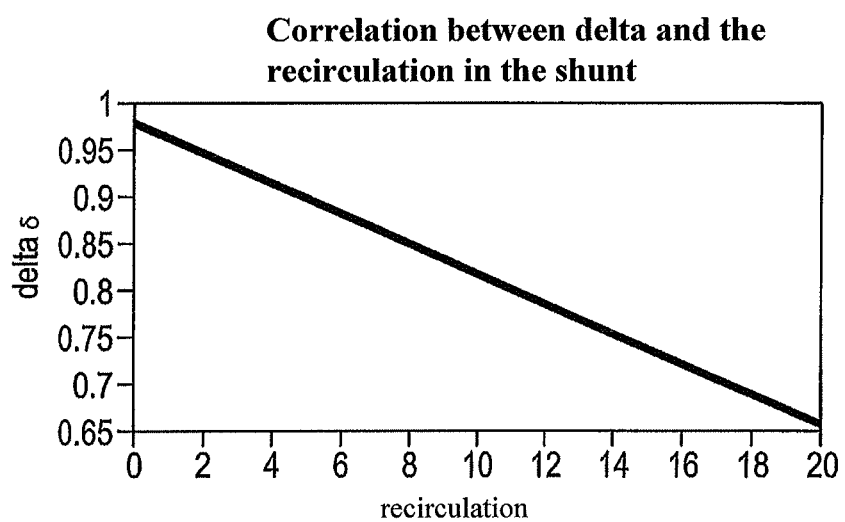
FIG. 5 shows a diagram for the correlation between damping δ and recirculation in the shunt.
Figure 8:
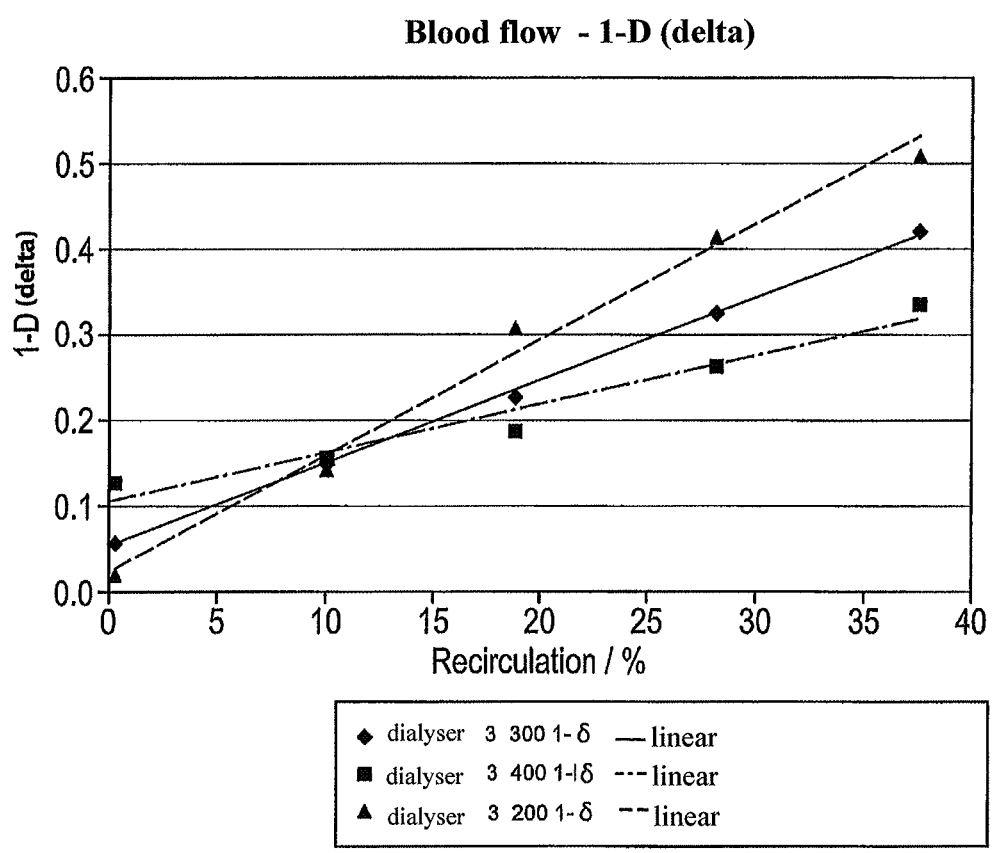
FIG. 8 is a diagram for the correlation of the recirculation and (1-δ) with different blood flows for a selected dialyser.

In order to obtain an increase >0 according to FIG. 8, 1−δ=1−D was applied to the y axis. FIG. 4 further shows the explained transient of the signal with and without recirculation. The correlation between the damping δ and the recirculation in the shunt is shown in FIG. 5.

Including the blood flow into the evaluating algorithm permits to select the appropriate characteristic line and thereby an increase in the accuracy of the determination of recirculation.

The transfer function from the determined value of the damping δ is thus possible by a polynomial which is of the first order, for example:

$$R = a \cdot (1-\delta)$$

Figure 6:
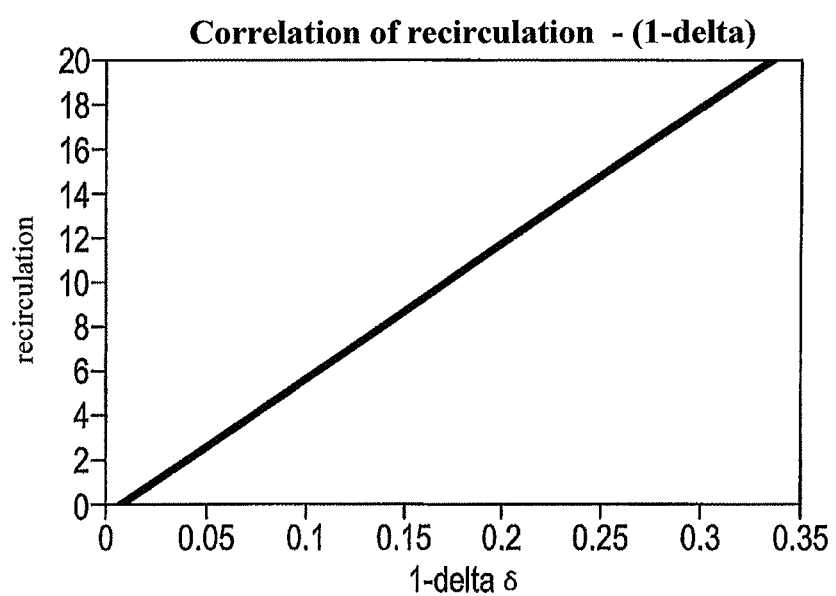
FIG. 6 shows a diagram for the correlation of the recirculation and (1-δ)

The correlation of the recirculation R with the term (1−δ) is shown in FIG. 6.

The transient behavior after a change of the blood flow depends on the dialyser 4 used in each case, i.e. especially on the volume of the dialyser 4 used, so that a characteristic line is resulting for each dialyser.

Figure 7:
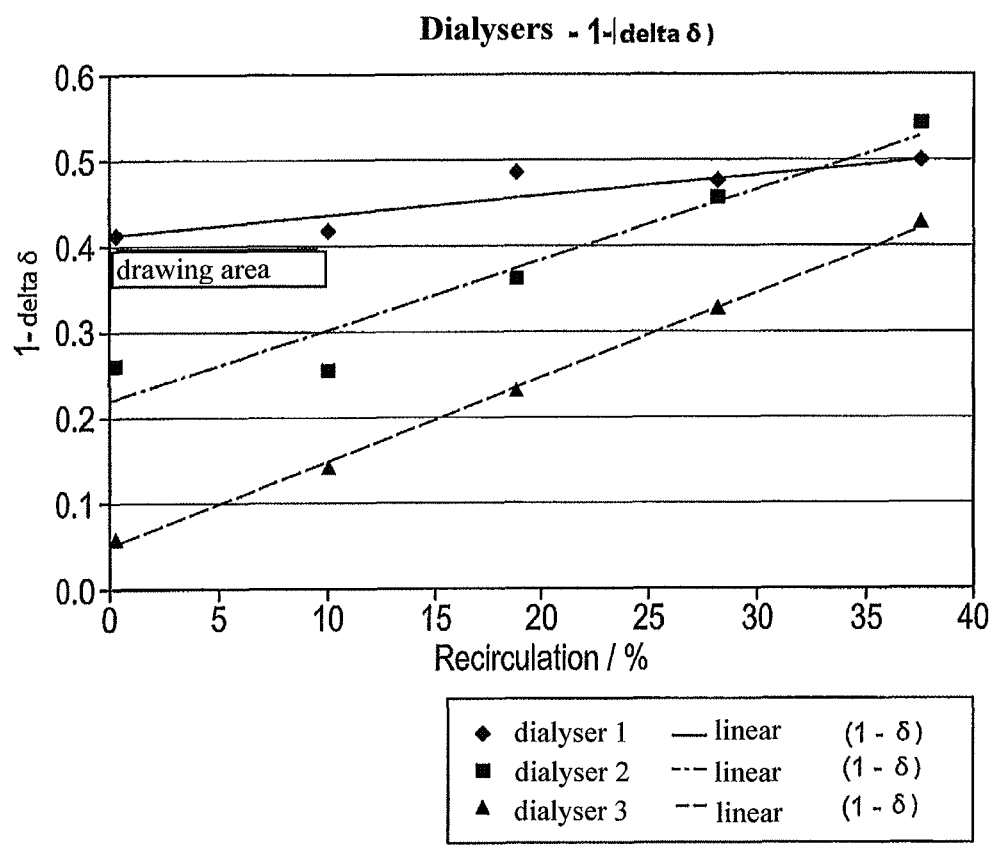
FIG. 7 shows dialyser recirculation characteristics for different dialysers.

Such family of characteristics is illustrated in FIG. 7. In order to obtain a positive increase 1−δ was applied to the y axis in FIG. 7. The knowledge of the type of dialyser is the prerequisite for an exact determination of the recirculation from the damping of the transfer function.

3.2 The Mathematic Determination of the Recirculation by Means of a Transient Method after a Change of the Blood Flow by the Integral Method As a parameter to be evaluated also the determined integral of the normalized time signal (intensity of the UV sensor 6) can be used.

Figure 9:
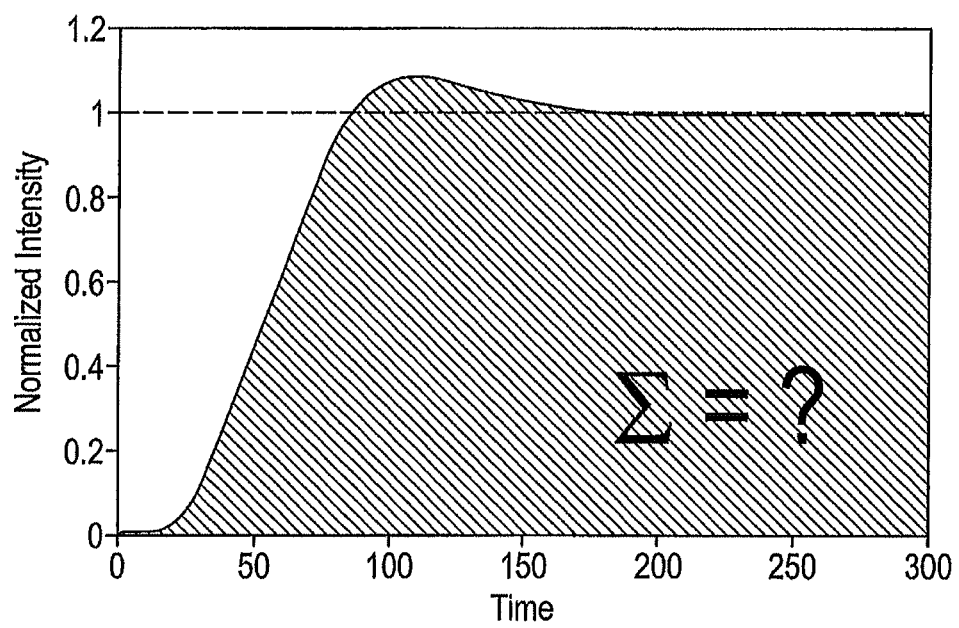
FIG. 9 is a diagram representation of the determined integral of the normalized time signal.

According to FIG. 9, between the defined times $t_1$ and $t_2$ a normalized intensity, i.e. the 0 value of the signal before the change of the blood flow, the 1 value after the transient to the higher signal level, is added.

FIG. 9 shows an example in which:

$t_1 = 0$ s related to the start of the triggered change of the blood flow and $t_2 = 300$ s related to the start of the triggered change of the blood flow.

The integral or the sum can be established numerically or analytically by techniques well known to those skilled in the art, in the exemplary case:

$$\text{``Größen'' variable} \ldots G\text{''} = \sum_{t=t_1}^{t=t_2} Detektor_t$$

("variable.G") (detector$_t$)

wherein detector$_t$=measured intensity in the UV sensor 6 at the time t.

Figure 10:
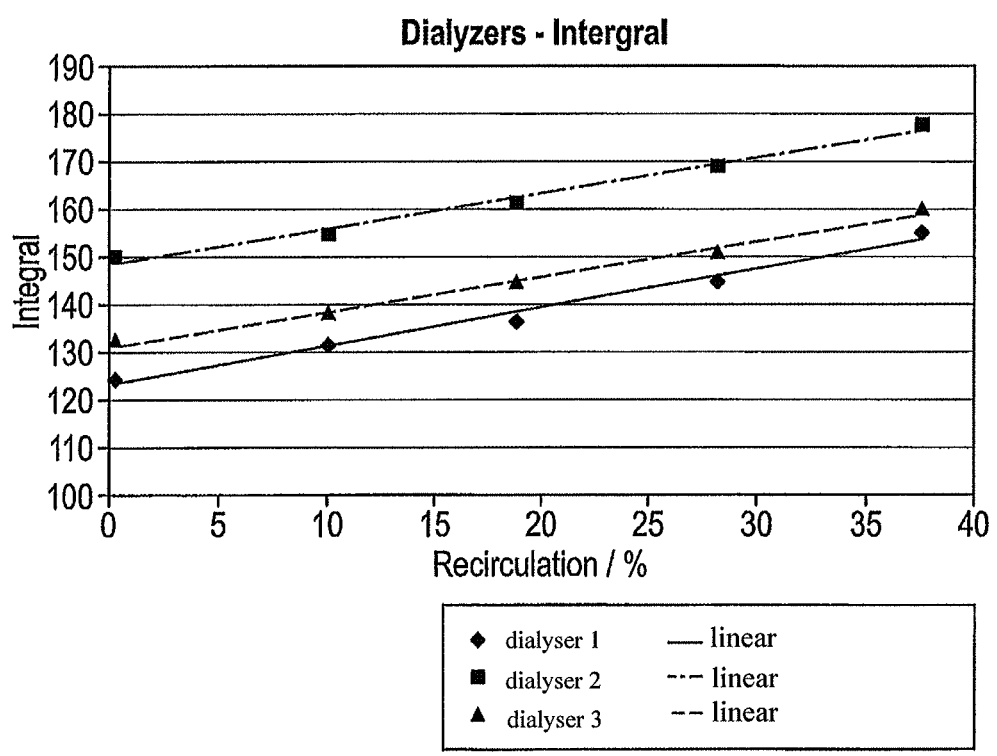
FIG. 10 is a diagram representation of the correlation between the integral and the recirculation for different dialysers.

Also the transient analysis by means of the integral method in turn is based on the principle illustrated with respect to the damping δ that from a "dilution" in the arterial tubing system of the proximal circulatory branch and thus stoppage (also start depending on the direction of change of the blood flow) of an existing recirculation overshooting of the time signal used is resulting. The principle is illustrated in FIG. 4. The value adopted by the "variable" in the integral method is directly proportional to the recirculation level so that a function is resulting for the relation between the recirculation R and the integral/sum which can be approximated, for example, by a first-order polynomial. This relation is graphically shown in FIG. 10. In this case, too, the "variable" (the integral in this example) depends on the dialyser used, which is equally illustrated in FIG. 10.

Figure 11:
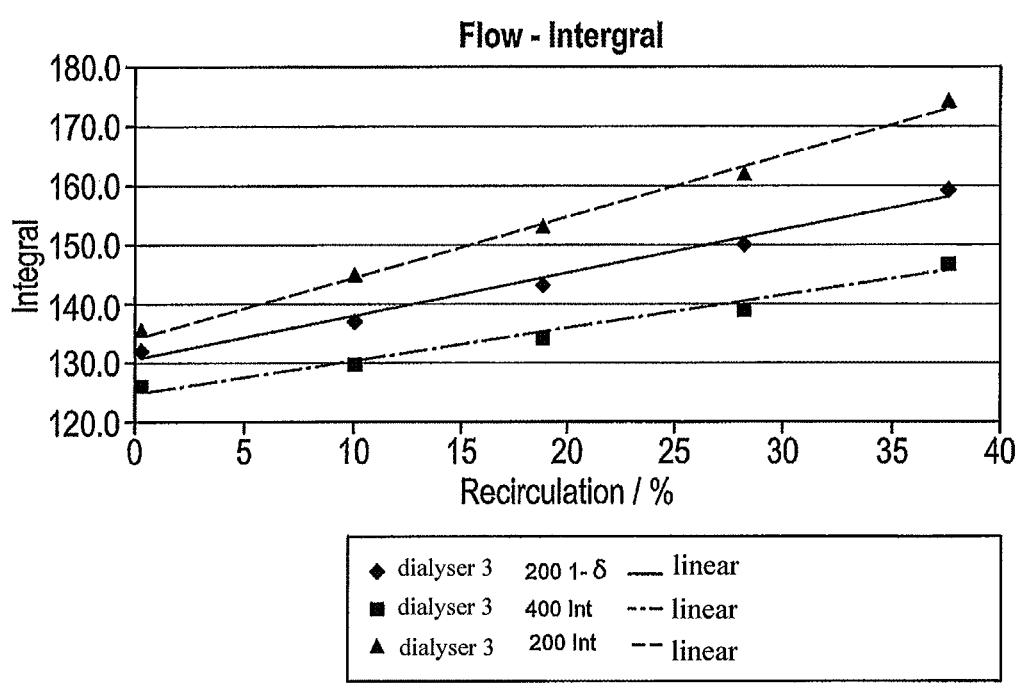
FIG. 11 is a diagram representation of the dependence of the integral on the blood flow.

It is graphically shown in FIG. 11 that also the integral (just as the damping δ) is dependent on the blood flow. This has an effect on the gradient and the offset of the functional relation which in the exemplary case is approximated by a first-order polynomial. In the case of the integral method, too, the measuring accuracy could be increased by an empirically established correcting factor by limitation of the blood-side concentration range, when the value of absorption measured at BF=50 ml/min is additionally considered for the evaluation.

It is obvious to those skilled in the art that the knowledge of the dialyser used and of the blood flow definitely improves the determination of the recirculation, because in this way the correct functional relation can be established between the variable (integral) and the recirculation.

Hereinafter an exemplary embodiment shall be illustrated:

The use of the partial integral as "variable", which is proportional to the recirculation, in vitro shows the least scattering of the measuring results. In FIG. 9 this partial integral would be exemplary:

$$\text{"Größen variable ... G"} = \sum_{50s}^{150s} Detektor_t$$

3.3 The Mathematic Determination of the Recirculation by Means of a Transient Method after Change of the Blood Flow Over the Time Constant τ

Figure 12:
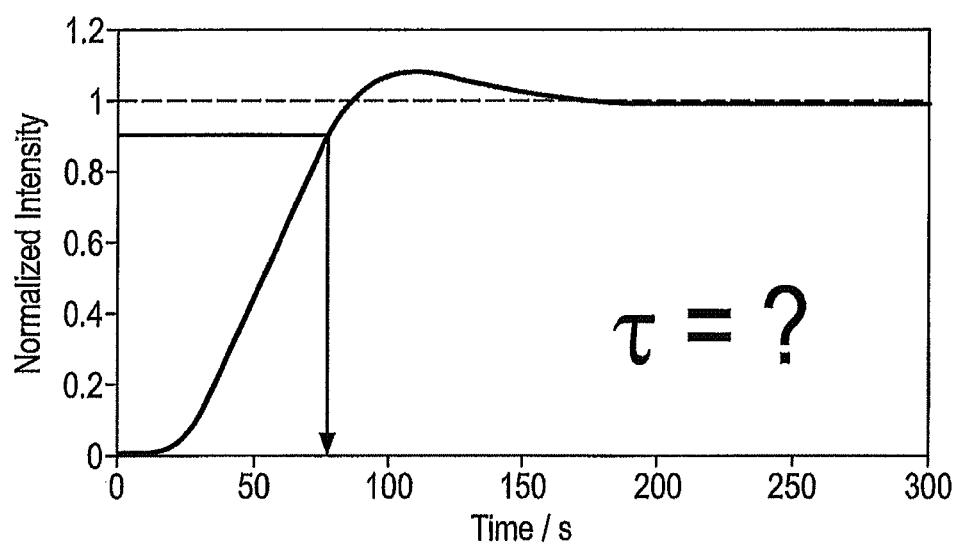
FIG. 12 is a diagram representation of the characteristic time τ of a signal increase.

Just as the damping δ or the integral, also a time constant τ can be used as parameter/"variable" for evaluating the time changes of the physicochemical parameter $P_D$:

The time constant τ is a characteristic time of the signal increase in the UV detector 6 after a change of the blood flow. By way of example, the time τ is used according to which a defined value $I_x$ of the normalized intensity signal [f(t)] is exceeded. In the exemplary case of the FIGS. 12 and 13 $I_x$=0.9 is applicable.

$\tau = \min(t)|f(t) > I_x$ is applicable.

Figure 13:
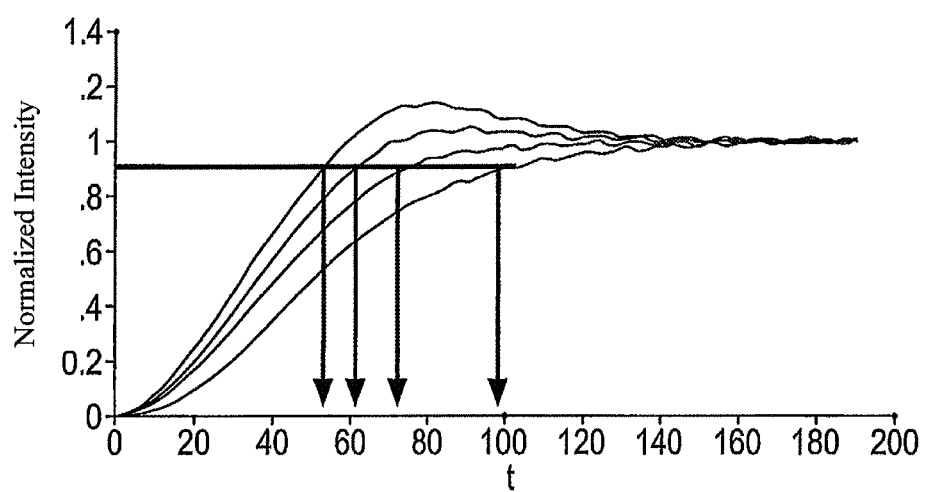
FIG. 13 is a diagram representation of the normalized intensity signals and the time constant τ at different recirculation levels.

FIG. 13 shows the normalized intensity signals at different recirculation levels. The higher the recirculation, the smaller the time constant τ—hence it is inversely proportional to the degree of recirculation.

Just as the damping δ and the determined integral over time, also the time constant τ is dependent on the dialyser used as well as on the second blood flow used.

Figure 14:
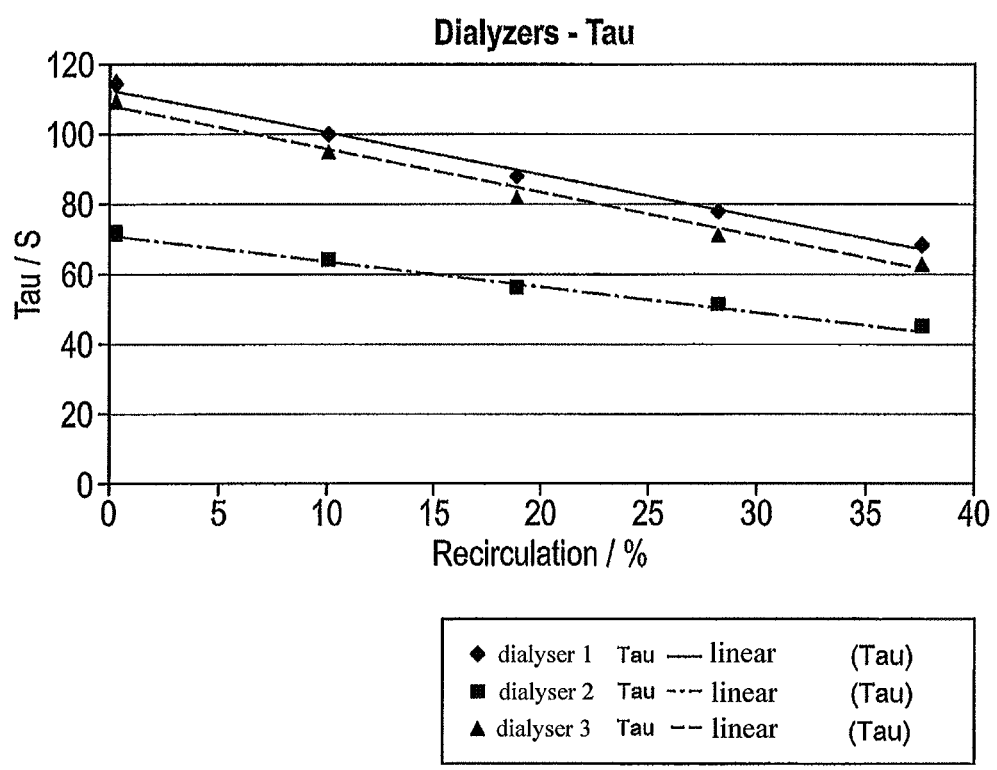
FIG. 14 is a diagram representation of the dependence of the time constant τ on the dialyser used.
Figure 15:
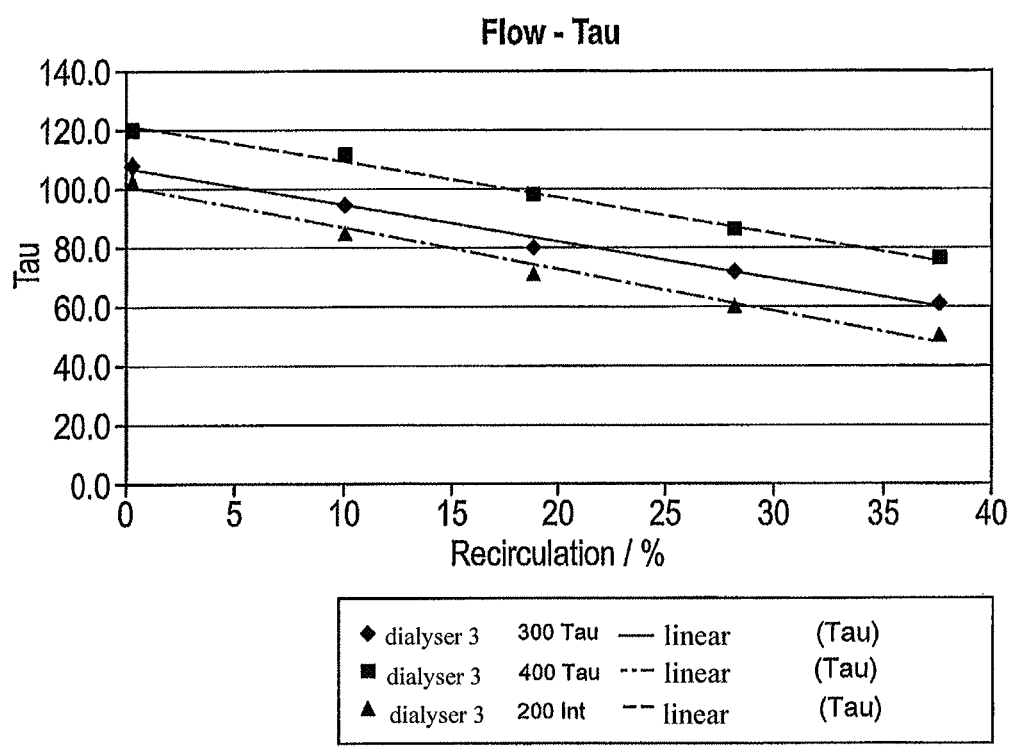
FIG. 15 is a diagram representation of the dependence of the time constant τ on the blood flow set.

In this embodiment of the invention, too, an increased measuring accuracy can be achieved by the knowledge of the UV absorption as a physicochemical parameter $P_D$ with a second blood flow of 50 ml/min, when the value for the recirculation measured with the aid of an empirically established factor is corrected. FIGS. 14 and 15 represent the influence of the blood flow and the dialyser on the time constant τ.

For each dialyser there exists a separate function which links the time constant τ to the recirculation R and, in the exemplary case, is represented as first-order polynomial. A change of the target blood flow in the case of "variable G"=τ causes a change of the offset as represented in FIG. 15 in terms of quality.

4. Identification of the Dialyser and Characteristic Diagrams

In general, "variable G"=f(dialyser, A, BF) is applicable to all methods of the transient analysis shown. These three parameters are known so that the recirculation R can be determined with the aid thereof from the dialysate-side measurement after a change of flow.

4.1 Identification of the Dialyser

In all described embodiments of the present invention the identification of the dialyser can be performed as follows:
  Input of the type of dialyser during measurement by the nursing staff
  Identification by means of RFID at the disposable
  Identification by means of barcode or DataMax reader at the disposable 4.2 Characteristic Diagrams Within the scope of practical implementation of the present invention it is of advantage to deposit a multi-dimensional function f(A, BF) for each dialyser being utilized so that with the aid of the known characteristic diagrams not only information as to quality is possible, i.e. a measurement of the type:

RECIRCULATION?→YES/NO, but—as explained in the foregoing—a determination as to quantity of the recirculation in the shunt can be performed.

All afore-mentioned methods (damping δ formation of integral and time constant τ) can be combined so as to increase the measuring accuracy by averaging the results obtained for the recirculation R or at least to carry out a plausibility check of the results. This course of action is possible as the methods provide results independent of each other. As a matter of course, those skilled in the art know that also an appropriately weighted averaging can be considered.

Those skilled in the art also know that, apart from the transient analysis methods by damping δ, formation of integral and time constant τ described by way of example, also further mathematical methods not described here are taken into account in order to calculate the recirculation in the shunt based on the time change of the parameter $P_D$ measured at the sensor 6 after change of the blood flow.

5. Modifications

The question whether recirculation is provided in the shunt vessel can be basically established also by a small change of the blood flow BF (referred to as $Q_b$ in the following equation). For this, the following relation is applicable:

$$C_e = \left( \frac{1-R}{1-R \cdot \left(1 - \frac{C_d}{Q_b}\right)} \right) \cdot C_d$$

wherein
$C_e$ is the effective clearance from the patient's viewpoint,
R is the recirculation and
$C_d$ is the clearance of the dialyser.

Figure 16:
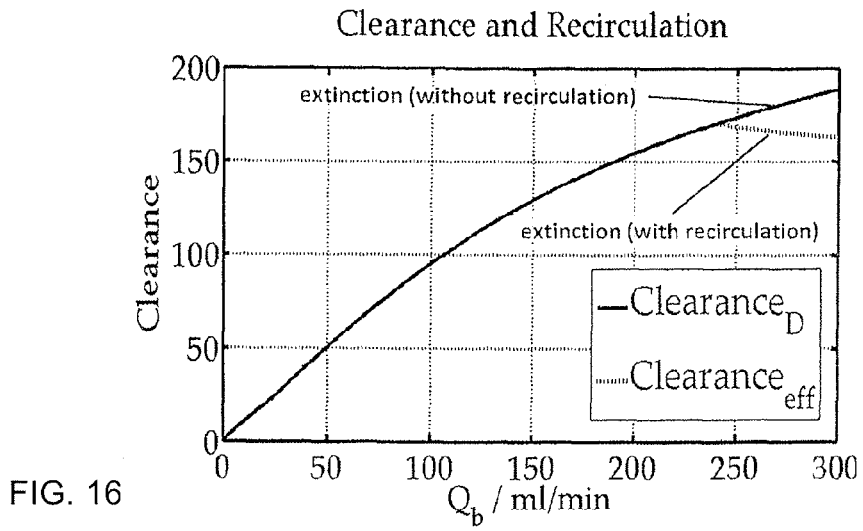
FIG. 16 is a clearance diagram in the case of a small change of the blood flow which calculates the relation of efficient clearance versus dialyser clearance diagrammatically in a model.

This means that the clearance by the recirculation effects at the patient's shunt falls definitely behind the pure dialyser clearance which would be provided in the case free of recirculation. This fact is illustrated by FIG. 16. Here the pure clearance characteristic line $K_1$ of a dialyser A is depicted. It applies to the case free of recirculation and also presents itself in this way from the patient's viewpoint for the case free of recirculation. $K_2$ represents the effective clearance when the latter was varied (reduced) by recirculation effects from the patient's viewpoint. In FIG. 16, by way of example it applies to $Q_B$=300 ml/min that R=20%.

Figure 17:
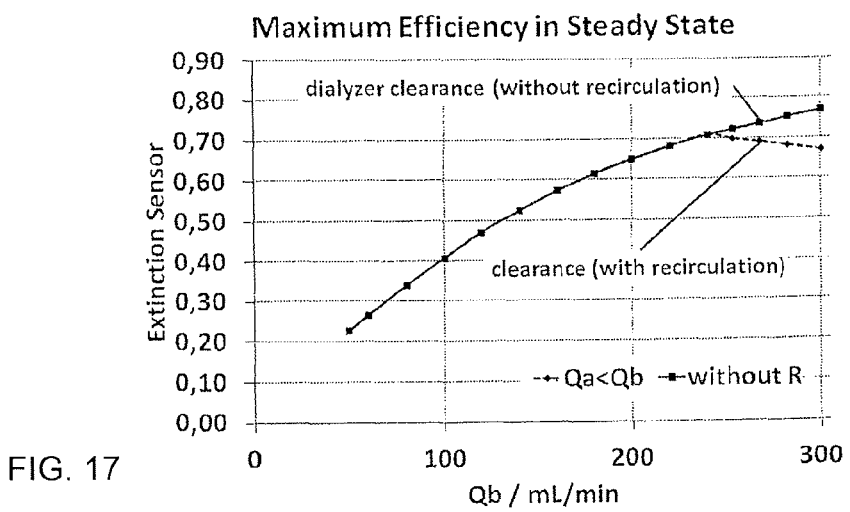
FIG. 17 diagrammatically measures the relation of efficient clearance versus dialyser clearance.

FIG. 17 shows the extinction (absorbance) measured by means of a UV sensor in the discharge of a dialysis machine. It is evident that the extinction is a direct measure for effective clearance. In FIG. 17 the extinction is applied in response to the blood flow for the case free of recirculation as well as for the recirculation case. Also in this case, by way of example, the precondition was assumed that R (recirculation) adopts a value of 20% with a blood flow of 300 ml/min.

Figure 18:
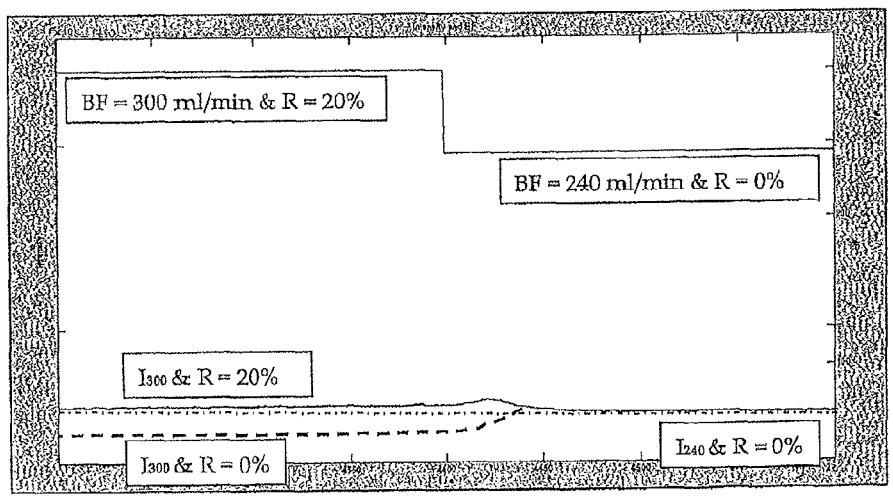
FIG. 18 is a diagram representation of an example of a change of absorption with a small change of the blood flow.

If one intends to find out with a blood flow $Q_{b1}$ whether recirculation is prevailing, this can be done by indicating a small change of the blood flow (e.g. $Q_{b1}$+/−40 ml/min). Then the variation of extinction/intensity is monitored at the UV sensor. FIG. 18 shall illustrate by an example how this principle is working. The present example according to FIG. 18 takes the following assumption as a basis:
  I. $Q_b$=300 ml/min for R=0% or R=20%
  II. $Q_{shunt}$=240 ml/min for R=20%
  III. $Q_{shunt}$=300 ml/min for R=0%
Depending on the initial state, the intensity varies in a particular way depending on whether or not R>0%. In this way monitoring of the increase after a change of the blood flow may provide the information whether or not recirculation was provided. The signal analysis is made by methods known to those skilled in the art (e.g. HillClimber, search for change of sign in the signal, ratio of stationary levels etc.).

Consequently, a control method of a dialysis machine as well as a dialysis machine for permitting the dialysate-side detection of a recirculation in an arteriovenous shunt of a patient during ongoing hemodialysis is described, wherein the dialysis machine comprises at least one dialysis fluid inlet (1) as well as at least one dialysis fluid discharge (2) for a selected dialysis fluid and at least one dialysis fluid pump (3) which are in fluidic communication with at least one dialyser (4) having a semipermeable membrane that forms the boundary between the dialysis fluid side and a blood side of the dialysis machine, wherein the dialysis fluid on the dialysis fluid side of the membrane flows through a dialysis fluid chamber (4a) of the dialyser (4) in a predetermined direction and wherein on the blood side of the dialysis machine blood is guided in an extracorporeal circulatory branch through a blood chamber (4b) of the dialyser (4) by means of a blood pump (5) in a direction opposite to the flow direction of the dialysis fluid so as to remove uremic toxins by diffusion via the semipermeable membrane from the extracorporeal-guided blood,
wherein a sensor (6), viewed in the flow direction of the dialysis fluid, is connected downstream of the dialyser (4) and detects a change of a physicochemical parameter $P_D$ of the outflowing dialysis fluid; and control elements (8, 9) are provided to guide the dialysis fluid in a selected manner through the dialyser (4) or to pass it by the latter, comprising the following process steps (or dialysis machine functions):
- (means for) optionally passing the dialysis fluid by the dialyser (4) so that the dialysis fluid is guided unchanged along the sensor (6), whereby the sensor (6) is calibrated by the pure dialysis fluid;
- (means for) switching the control elements (8, 9) after optimum sensor calibration such that the dialysis fluid flows through the dialyser chamber (4a), and setting a desired first blood flow value $BF_1$ in the blood-side extracorporeal circulatory branch such that a recirculation R adjusts between the inlet (20) of the extracorporeal circulatory branch and an outlet (21) of the extracorporeal circulatory branch and a first clearance $K_1$ is adjusted via the semipermeable membrane of the dialyser (4) and the parameter detected by the sensor (6) adopts an appropriate value $P_{D1}$;
- (means for) changing the first blood flow value $BF_1$ to a desired second blood flow value $BF_2$, wherein a second clearance $K_2$ is adjusted via the semipermeable membrane of the dialyser (4); and a new parameter value $P_{D2}$ as well as the course of change from $P_{D1}$ to $P_{D2}$ is appropriately provided and detected; and
- (means for) determining the recirculation R by way of the course of change (and/or the change) from the parameter value $P_{D1}$ to the parameter value $P_{D2}$.

The invention claimed is:
1. A control method of a dialysis machine to allow detection on the dialysis fluid side of recirculation in an arteriovenous inlet/outlet element, preferably a shunt, wherein the dialysis machine comprises at least one dialysis fluid inlet and at least one dialysis fluid discharge for a selected dialysis fluid and at least one dialysis fluid pump which are in fluidic communication with at least one dialyser, wherein, viewed in the dialysis fluid flow direction, a sensor is arranged downstream of the dialyser and detects a change of a physico-chemical parameter ($P_D$) of the outflowing dialysis fluid, the method comprising the steps of:
setting a desired first blood flow value $BF_1$ at which recirculation R>/=0 is adjusted and the parameter detected by the sensor adopts an appropriate value $P_{D1}$;
changing the first blood flow value $BF_1$ to a preferably lower second blood flow value $BF_2$, wherein at the sensor a new parameter value $P_{D2}$ is appropriately provided and detected;
determining recirculation R by way of the course of change and/or the change from the parameter value $P_{D1}$ to the parameter value $P_{D2}$; wherein the physicochemical parameter $P_D$ is an optical absorption, and wherein an absorption in the IR wavelength range, UV wavelength range or in the visible wavelength range, or an absorbance is utilized.

2. The method according to claim 1, wherein the UV wavelength range has a wavelength of approx. 280 nm and a UV detector is used as sensor.

3. The method according to claim 1, wherein the second blood flow value $BF_2$ is lower than the first blood flow value $BF_1$, wherein it is especially applicable: $BF_2=r \times BF_1$, wherein r=0.05 to 0.595; or that the second blood flow value $BF_2$ is higher than the first blood flow value $BF_1$, wherein especially $BF_2=r \times BF_1$ is applicable, with r=1.05 to 20.

4. The method according to claim 1, wherein the recirculation R is detected by a transient behavior of the time course of the change of the physicochemical parameter $P_D$ after change of the first blood flow $BF_1$ to the second blood flow $BF_2$ or vice versa.

5. The method according to claim 4, wherein the transient behavior is detected by a damping δ and the recirculation R is determined by means of the damping δ of the transient behavior after applying the second blood flow $BF_2$.

6. The method according to claim 4, wherein the transient behavior is detected after applying the second blood flow $BF_2$ by integrating a normalized time signal, especially having an intensity output by the sensor, over a particular time range and hereby the recirculation R is determined.

7. The method according to claim 4, wherein the transient behavior is detected after applying the second blood flow $BF_2$ by a characteristic time τ of a signal increase of the output signal supplied by the sensor and hereby the recirculation R is determined.

8. A dialysis machine comprising means for detecting recirculation in an arteriovenous inlet/outlet element, preferably a shunt, wherein the dialysis machine has a dialysis fluid side and a blood side; wherein
on the dialysis fluid side at least one
dialysis fluid inlet as well as at least one
dialysis fluid discharge for a selected dialysis fluid is provided which are in fluidic communication with at least one dialyser, and comprising
at least one sensor for detecting and preferably storing a course of change and/or a change of a physicochemical parameter $P_D$ of the dialysis fluid outflowing from the dialyser, wherein
the dialysis machine is adapted to a desired first blood flow value $BF_1$ being adjustable in the blood-side extracorporeal circulatory branch, whereby between an inlet of the extracorporeal circulatory branch and an outlet of the extracorporeal circulatory branch a recirculation R>/=0 is adjusted and the parameter detected by the sensor adopts an appropriate value $P_{D1}$;
the first blood flow value $BF_1$ is adapted to be changed to a second blood flow value $BF_2$ and thus at the sensor a corresponding new parameter value $P_{D2}$ is provided; and means are provided which are adapted to detect the course of change and/or the change from the parameter value $P_{D1}$ to the parameter value $P_{D2}$ and to determine therefrom the recirculation R according to a method according to claim 1.

9. The dialysis machine according to claim 8, wherein the UV wavelength range has a wavelength of approx. 280 nm and the sensor is a UV detector.

10. The dialysis machine according to claim 8, wherein the second blood flow value $BF_2$ is lower than the first blood flow value $BF_1$, wherein preferably $BF_2=r\times BF_1$ is applicable, with r=0.05 to 0.95; or the second blood flow value $BF_2$ is higher than the first blood flow value $BF_1$, wherein preferably $BF_2=r\times BF_1$ is applicable, with r=1.05 to 20.

11. The dialysis machine according to claim 8, wherein the transient behavior of the time course of the change of the physicochemical parameter $P_D$ after change of the first blood flow $BF_1$ to the second blood flow $BF_2$ is a measure for the recirculation R.

12. The dialysis machine according to claim 11, wherein the transient behavior is detected or detectable by a damping $\delta$ and by means of the damping $\delta$ of the transient behavior after applying the second blood flow $BF_2$ the recirculation R is calculated or can be calculated by means of a processor.

13. The dialysis machine according to claim 11, wherein the transient behavior is detected or detectable after applying the second blood flow $BF_2$ by integration of a normalized time signal, preferably an intensity output by the sensor, over a definite time range and hereby the recirculation R is calculated or can be calculated by a processor.

14. The dialysis machine according to claim 11, wherein the transient behavior is detected or detectable after applying the second blood flow $BF_2$ by a characteristic time $\tau$ of a signal increase of the output signal supplied by the sensor and hereby the recirculation R is calculated or can be established by a processor.

15. The dialysis machine according to claim 8, wherein pressure sensors are provided in the proximal circulation for the arterial pressure (PA), the venous pressure (PV) and the entrance pressure (PBE) for the dialyser.

* * * * *